United States Patent
Kim et al.

(10) Patent No.: US 9,895,123 B2
(45) Date of Patent: Feb. 20, 2018

(54) APPARATUS FOR GENERATING X-RAY IMAGE AND METHOD THEREOF

(71) Applicant: SAMSUNG ELECTRONICS CO., LTD., Suwon-si (KR)

(72) Inventors: Sung Su Kim, Yongin-si (KR); Hyun Hwa Oh, Hwaseong-si (KR); Jae Hyun Kwon, Hwaseong-si (KR); Young Hun Sung, Hwaseong-si (KR); Kang Eui Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 421 days.

(21) Appl. No.: 14/560,404

(22) Filed: Dec. 4, 2014

(65) Prior Publication Data

US 2015/0150528 A1 Jun. 4, 2015

(30) Foreign Application Priority Data

Dec. 4, 2013 (KR) ........................ 10-2013-0149878

(51) Int. Cl.
*A61B 6/00* (2006.01)
*G06T 5/00* (2006.01)
*G06T 5/40* (2006.01)

(52) U.S. Cl.
CPC ............ *A61B 6/5205* (2013.01); *A61B 6/488* (2013.01); *A61B 6/502* (2013.01); *A61B 6/545* (2013.01); *G06T 5/007* (2013.01); *G06T 5/40* (2013.01); *G06T 2207/10116* (2013.01); *G06T 2207/20104* (2013.01); *G06T 2207/30068* (2013.01)

(58) Field of Classification Search
CPC ...................... A61B 6/502; G06T 2207/30068
See application file for complete search history.

(56) References Cited

U.S. PATENT DOCUMENTS

2009/0185733 A1* 7/2009 Heinlein ................ A61B 6/502
382/132
2011/0075791 A1* 3/2011 Nakayama ............. A61B 6/022
378/4

* cited by examiner

*Primary Examiner* — Dani Fox
(74) *Attorney, Agent, or Firm* — Sughrue Mion, PLLC

(57) ABSTRACT

A method and apparatus for generating an X-ray image are provided. The method includes obtaining an X-ray image of an object, performing image analysis on a tissue of interest in an area other than an interference target region in the obtained X-ray image, and performing image processing on an entirety of the obtained X-ray image based on information on the analyzed tissue of interest and generating a final X-ray image.

14 Claims, 13 Drawing Sheets

APPARATUS FOR GENERATING X-RAY IMAGE AND METHOD THEREOF

CROSS-REFERENCE TO RELATED APPLICATION

This application claims priority to Korean Patent Application No. 10-2013-0149878, filed on Dec. 4, 2013 in the Korean Intellectual Property Office, the disclosure of which is incorporated herein by reference in its entirety.

BACKGROUND

1. Field

Apparatuses and methods consistent with the exemplary embodiments relate to a method of generating an X-ray image and an apparatus therefor, and more specifically, to a method of generating an X-ray image that generates an X-ray image of a breast and an apparatus therefor.

2. Description of the Related Art

X-rays are radiated onto a specific material and are transmitted according to physical characteristics of tissues, structures, or physical materials inside of an object for example, a density of the material, or absorbed and attenuated by the material, at a constant rate. An X-ray imaging apparatus obtains an image of an internal structure, tissue, or material of a specific object. An image is obtained when X-rays are transmitted through or are absorbed by the internal structure, tissue, or material of a specific object and are attenuated by materials in the internal structure, tissue, or material of a specific object.

Specifically, the X-ray imaging apparatus radiates X-rays onto an object, detects X-rays transmitted through the object or radiated near the object, and then generates an X-ray image of an internal structure, tissue, or material of the object based on the detected X-rays. Since an X-ray imaging apparatus can be used to verify an internal structure, tissue, or the like of an object through an image as described above, it can be used by doctors to detect abnormalities such as lesions inside a human body, to identify internal structures of objects or components in a field of industry, and to scan the contents of luggage in airports.

X-ray imaging apparatuses include general X-ray imaging apparatuses, computed tomography (CT) apparatuses, breast imaging apparatuses, and the like.

SUMMARY

The exemplary embodiments provide a method of generating an X-ray image that increases precision and accuracy with respect to a tissue of interest which is important for imaging and generates a high quality diagnostic X-ray image, and an apparatus therefor.

According to an aspect of an exemplary embodiment, there is provided a method of generating an X-ray image. The method includes obtaining an X-ray image of an object, performing image analysis on a tissue of interest in an area other than an interference target region in the obtained X-ray image, and performing image processing on an entirety of the obtained X-ray image based on information on the analyzed tissue of interest and generating a final X-ray image.

According to another aspect of an exemplary embodiment, there is provided an apparatus for generating an X-ray image. The apparatus includes an X-ray source configured to radiate X-rays onto an object, an X-ray detecting assembly configured to detect X-rays transmitted through the object and convert the detected X-rays into an electrical signal, and an image processor configured to generate an X-ray image by reading the electrical signal, perform image analysis on a tissue of interest in an area other than an interference target region in the generated X-ray image, perform image processing on the entire X-ray image based on analyzed information, and generate a final X-ray image.

BRIEF DESCRIPTION OF THE DRAWINGS

These and/or other aspects of an exemplary embodiments will become apparent and more readily appreciated from the following description of the exemplary embodiments, taken in conjunction with the accompanying drawings of which.

DETAILED DESCRIPTION

Figure 1:
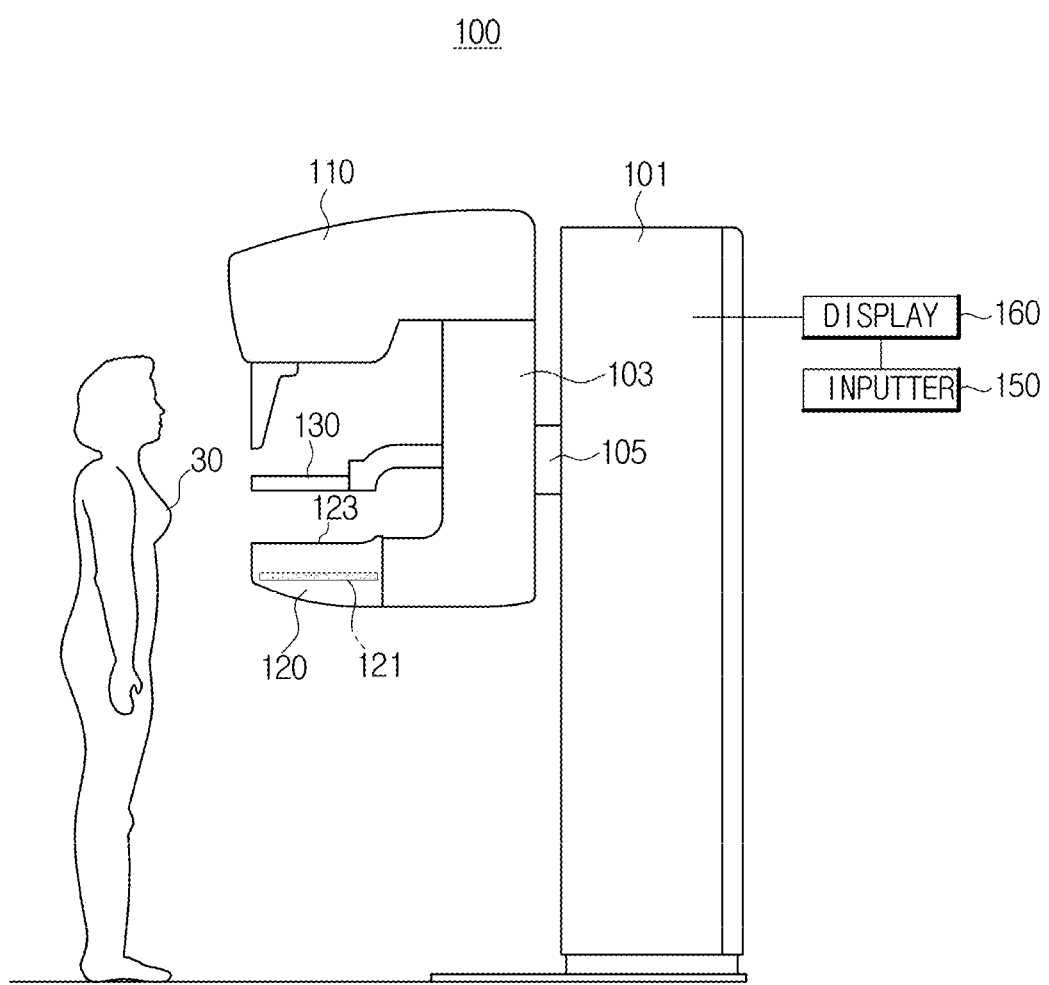
FIG. 1 is a diagram illustrating an appearance of an apparatus for generating an X-ray image according to an exemplary embodiment.

Purposes, specific advantages, and novel features of the exemplary embodiments will be apparent from the descriptions of the exemplary embodiments and the following detailed descriptions related to the accompanying drawings. In this specification, when reference numerals are assigned to components of each drawing, it should be noted that, when the same components are illustrated in different drawings, the same numerals are assigned to the same components whenever possible. In descriptions of an exemplary embodiment, when detailed descriptions of related well-known technology are deemed to unnecessarily obscure the description of an exemplary embodiment, they will be omitted. In this specification, although the terms first, second, etc. are used to distinguish one component from another, these components are not limited by these terms.

Hereinafter, exemplary embodiments will be described in detail with reference to the accompanying drawings. In each drawing, the same component will be denoted with the same reference numeral. Hereinafter, the exemplary embodiments will be described with respect to an apparatus for generating an X-ray image for imaging a breast as an example, but the exemplary embodiments are not specifically applied to only breast imaging. It will be apparent that the invention also can be applied to a general apparatus for generating an X-ray image.

FIG. 1 is a diagram illustrating an appearance of an apparatus for generating an X-ray image according to an exemplary embodiment.

As illustrated in FIG. 1, an apparatus for generating an X-ray image 100 according to the exemplary embodiment may include an X-ray source 110, an X-ray detecting assembly 120, and a compression paddle 130.

The X-ray source 110 and the X-ray detecting assembly 120 may be connected to a frame 103 so as to face each other. The frame 103 may be connected to a main body 101 through an arm 105. The arm 105 moves in a vertical direction in order to match a height of a subject, or rotates at a predetermined angle, which allows the apparatus for generating an X-ray image 100 to obtain a tomographic image or a 3D image of an object.

The apparatus for generating an X-ray image 100 according to the exemplary embodiment may be used to image a breast and generate an X-ray image of the breast. That is, an object 30 can be, for example, a human breast. Here, the object 30 refers to a region of a subject, such as a patient, serving as a diagnostic target to be examined by using the apparatus for generating an X-ray image 100 and the subject may be a living body such as a human body.

When X-ray imaging is performed on the breast, the breast is the object 30 positioned between the X-ray source 110 and the X-ray detecting assembly 120, and X-rays which are transmitted through the breast among X-rays radiated from the X-ray source 110 are detected by the X-ray detecting assembly 120.

The X-ray detecting assembly 120 serves as a support or a table for supporting the breast and is also called a bucky. The X-ray detecting assembly 120 includes an X-ray detector 121 located inside of the X-ray detecting assembly 120 for detecting X-rays, and may include the breast contactor 123 that comes in contact with the breast. The breast contactor 123 may be made of a material having high X-ray permeability and may be implemented by, for example, a carbon sheet.

The apparatus for generating an X-ray image that images the breast may have different structural features from a general apparatus for generating an X-ray image due to characteristics of breast tissue. One of the features of an apparatus for generating an X-ray image of a breast is the compression paddle 130 for compressing the breast, as illustrated in FIG. 1.

That is, when the breast is lifted onto a breast contactor 123 of the X-ray detecting assembly 120, a user manipulates an inputter 150 (refer to FIG. 4) to move the compression paddle 130 in a vertical direction and thus the breast which is placed on the breast contactor 123 may be compressed. Here, the user may be medical staff, such as a doctor, a radiologist, or a nurse, who performs diagnosis of the object using the apparatus for generating an X-ray image 100, but the user is not limited thereto and may include anyone who uses the apparatus for generating an X-ray image.

As such, after the breast is compressed using the compression paddle 130, imaging is performed. Imaging is performed to reduce an X-ray exposure dose on the breast and to obtain a clear X-ray image of the breast. A description thereof will be provided in detail with reference to FIGS. 2 and 3.

Figure 2:
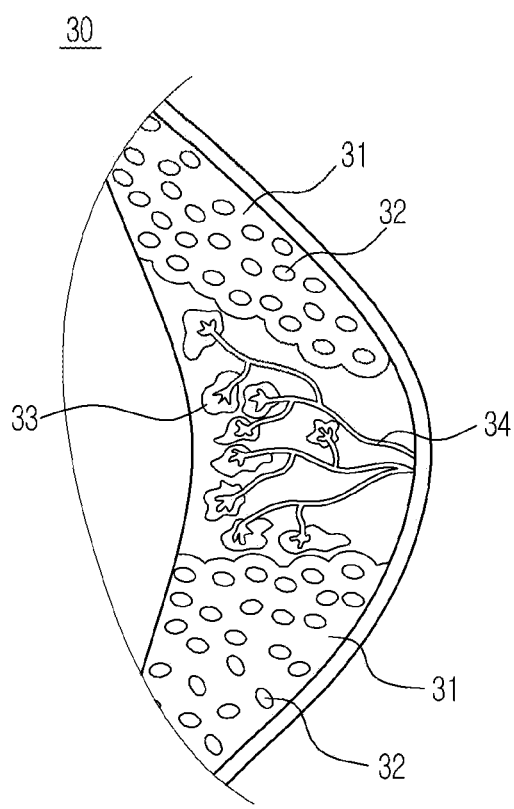
FIG. 2 is a diagram illustrating an internal structure of a breast.

FIG. 2 is a diagram illustrating an internal structure of the breast.

As illustrated in FIG. 2, tissues of the breast, which is the object 30 include a fibrous tissue 31 that surrounds a circumference of the breast and maintains its shape, a fat tissue 32 that is distributed throughout the whole breast, a mammary tissue 33 that produces milk, and a lactiferous duct 34 that is a path through which the milk passes, and the like. Of the tissues, tissues related to production and supply of the milk, such as the mammary tissue 33 and the lactiferous duct 34, are referred to as fibroglandular tissues.

An attenuation coefficient is data indicating a degree of attenuation as X-rays are transmitted. Since the attenuation coefficient differs according to materials constituting the inside of the object 30, it is possible to image the inside of the object 30 based on a degree of transmitted X-rays.

Figure 3:
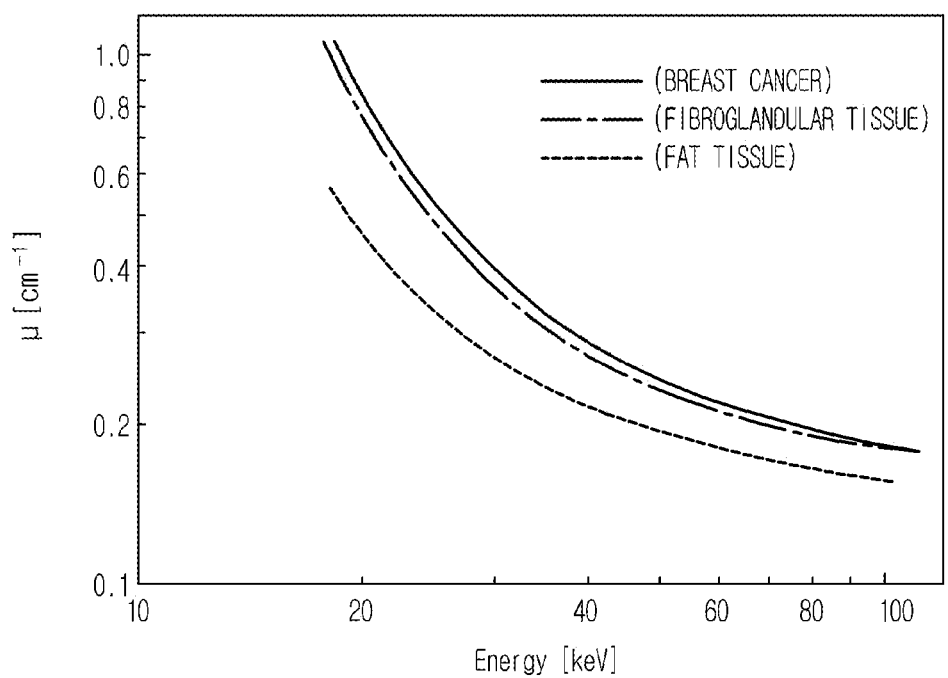
FIG. 3 is a graph illustrating an attenuation coefficient of each material making up the inside of the breast for each energy band.

FIG. 3 is a graph illustrating an attenuation coefficient of each material constituting the inside of the breast for each energy band. Here, the material constituting the inside of the breast may be specifically understood as breast cancer, fibroglandular tissues, and fat tissues.

As illustrated in FIG. 3, a difference between attenuation coefficients of materials constituting the breast is not great. This is because the breast is composed of only soft tissues, as shown in FIG. 2. In order to obtain the clearest X-ray image, the aforementioned compression paddle 130 is used to reduce a thickness of the breast. In this manner, the breast is compressed and becomes thinner so that materials constituting the breast do not overlap but are spread in a direction in which X-rays are radiated. Therefore, it is possible to increase the quality of an X-ray image to be generated and also decrease the X-ray exposure to the breast.

Referring again to FIG. 1, the compression paddle 130 is mounted on the frame 103 that connects the X-ray source 110 and the X-ray detecting assembly 120 and can move in a vertical direction. In order to perform X-ray imaging, the breast serving as the object 30 is placed on the breast contactor 123 of the X-ray detecting assembly 120, the user moves the compression paddle 130 down using the inputter 150 and compresses the breast, X-rays are radiated onto the breast while the breast is compressed, and X-ray imaging for detecting X-rays transmitted through the breast is performed.

The appearance of the apparatus for generating an X-ray image 100 according to the exemplary embodiment has been described above. Hereinafter, each configuration of the apparatus for generating an X-ray image 100 according to the exemplary embodiment will be described.

Figure 4:
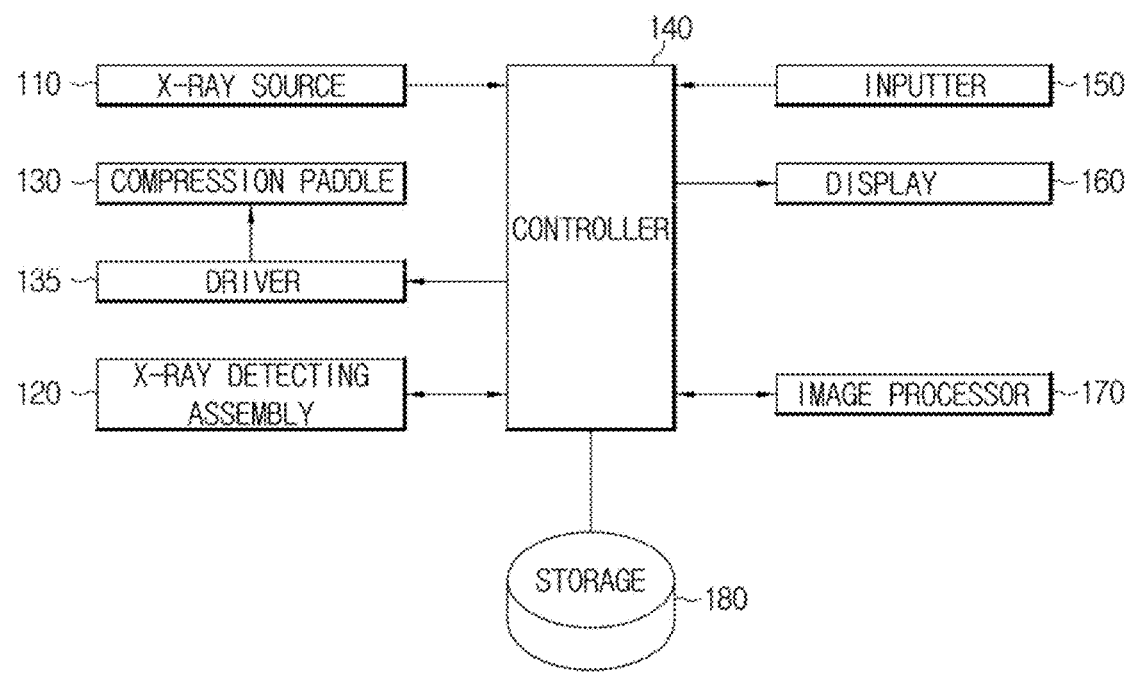
FIG. 4 is a block diagram illustrating a configuration of the apparatus for generating an X-ray image according to the exemplary embodiment.

FIG. 4 is a block diagram illustrating a configuration of an apparatus for generating an X-ray image 100 according to the exemplary embodiment.

As illustrated in FIG. 4, the apparatus for generating an X-ray image 100 according to the exemplary embodiment may include the X-ray source 110, the X-ray detecting assembly 120, the compression paddle 130, a driver 135, a controller 140, the inputter 150, a display 160, and an image processor 170.

Figure 5:
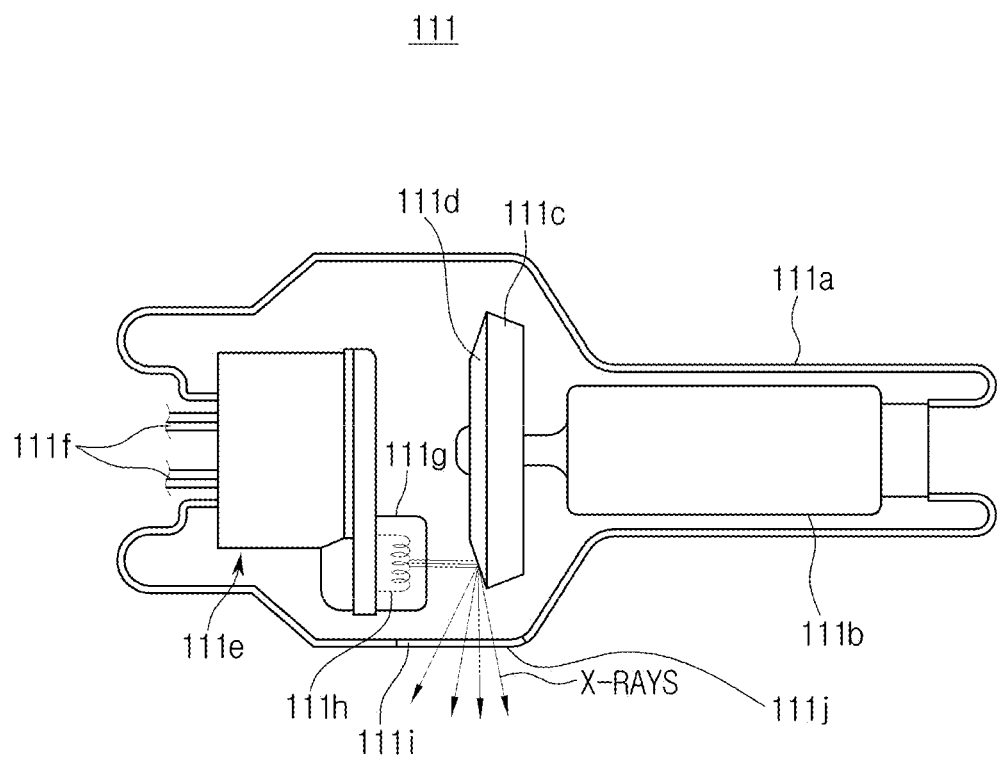
FIG. 5 is a diagram schematically illustrating a structure of an X-ray tube, in accordance with an exemplary embodiment.

The X-ray source 110 includes an X-ray tube 111 configured to generate X-rays and is referred to as an X-ray tube head or an X-ray tube assembly. As illustrated in FIG. 5, the X-ray tube 111 may be implemented as a diode including an anode 111c and a cathode 111e and a tube body may be a glass tube 111a made of, for example, silica hard glass.

The cathode 111e includes a filament 111h and a focusing electrode 111g configured to focus electrons. The focusing electrode 111g is also referred to as a focusing cup. An inside of the glass tube 111a is maintained in a high vacuum state of about 10 mmHg, the filament 111h of the cathode is heated to a high temperature, and thermoelectrons are generated. A tungsten (W) filament may be used as an example of the filament 111h and the filament 111h may be heated by applying current to an electrical conductor 111f connected to the filament.

The anode 111c is mainly made of copper, and a target material 111d is coated or disposed on a side facing the cathode 111e. A high-resistance material such as chromium (Cr), iron (Fe), cobalt (Co), nickel (Ni), tungsten (W), and molybdenum (Mo) may be used as the target material. As a melting point of the target material increases, a focal spot size decreases.

When a high voltage is applied between the cathode 111e and the anode 111c, thermoelectrons are accelerated and collide with the target material 111d of the anode, and thus X-rays are generated. The generated X-rays are radiated externally through a window 111i and a beryllium (Be) film may be used as a material of the window. In this case, a filter 111j is positioned in a front surface or a rear surface of the window 111i and thus X-rays of a specific energy band may be filtered.

The target material 111d may be rotated by a rotor 111b. When the target material 111d is rotated, a heat accumulation rate per unit area may be ten times or more that of a fixed state of the target material 111d and the focal spot size decreases.

Voltage applied between the cathode 111e and the anode 111c of the X-ray tube 111 is referred to as tube voltage, and a level thereof may be indicated as peak kilovaltage (kVp). As the tube voltage increases, a speed of the thermoelectrons increases. As a result, energy (photon energy) generated by the X-rays colliding with the target material 111d increases. Current flowing in the X-ray tube 111 is referred to as tube current and may be indicated as an average mA. As the tube current increases, the X-ray dose (the number of X-ray photons) increases.

Therefore, the X-ray energy may be controlled by the tube voltage, and a strength or a dose of X-rays may be controlled by the tube current and an X-ray exposure time. Energy and a strength of radiated X-rays may be controlled according to types or characteristics of the object 30.

When the radiated X-rays have a constant energy band, the energy band may be defined by an upper limit and a lower limit. The upper limit of the energy band, that is, maximum energy of radiated X-rays, may be adjusted by a level of the tube voltage. The lower limit of the energy band, that is, minimum energy of radiated X-rays, may be adjusted by the filter 111j. When X-rays of a low energy band are filtered using the filter, it is possible to increase average energy of the radiated X-rays.

Although not illustrated, the X-ray source 110 may further include a collimator disposed in a front surface of the window 111i. The collimator may adjust a radiation area of X-rays radiated from the X-ray tube 111 and reduces scattering of X-rays.

When X-rays are radiated onto the object 30 from the X-ray source 110, X-rays transmitted through the object 30 are detected by the X-ray detecting assembly 120. The X-ray detecting assembly 120 may include the X-ray detector 121 configured to detect X-rays.

In general, the X-ray detector 121 may be classified by a material configuration method, a method of converting detected X-rays into an electrical signal, and a method of obtaining an image signal.

First, the X-ray detector is classified as a single element configuration or a mixed element configuration depending on the material configuration method.

When the single element configuration is used, a part in which the X-rays are detected and an electrical signal is generated and a part in which the electrical signal is read and processed are made of a single element semiconductor or are manufactured in a single process. For example, a charge coupled device (CCD) or a complementary metal oxide semiconductor (CMOS) serving as a light receiving element is singly used.

When the mixed element configuration is used, a part in which the X-rays are detected and an electrical signal is generated and a part in which the electrical signal is read and processed are made of different elements or are manufactured in different processes. For example, there are cases in which X-rays are detected using a light receiving element such as a photo diode and cadmium zinc telluride (CdZnTe) and an electrical signal is read and processed using a CMOS read out integrated circuit (ROIC), a case in which X-rays are detected using a strip detector and an electrical signal is read and processed using a CMOS ROIC, and a case in which an amorphous-silicon (a-Si) or amorphous selenium (a-Se) flat panel system is used.

The X-ray detector may be classified as performing a direct converting method or an indirect converting method according to the method of converting X-rays into an electrical signal.

When X-rays are radiated, electron-hole pairs are temporarily generated inside the light receiving element, and electrons move to the anode and holes move to the cathode due to an electric field applied to both ends of the light receiving element. In the direct converting method, the X-ray detector converts this movement into an electrical signal. In the direct converting method, a-Se, CdZnTe, mercury(II) iodide ($HgI_2$), lead(II) iodide ($PbI_2$), or the like is used as a material of the light receiving element.

In the indirect converting method, a scintillator is provided between the light receiving element and the X-ray source. When X-rays radiated from the X-ray source react with the scintillator and photons having a wavelength of a visible light range are emitted, the light receiving element detects and converts the photons into an electrical signal. In the indirect converting method, a-Si or the like is used as a material of the light receiving element. A thin-film gadolinium oxysulfide (GADOX) scintillator, and a micro columnar or needle-shaped thallium doped cesium iodide (CSI TI) scintillator may be used as the scintillator.

A method of obtaining an image signal in the X-ray detector is classified as a charge integration mode in which electric charges are stored for a predetermined time and a signal is obtained therefrom or a photon counting mode in which photons having threshold energy or higher are counted whenever a signal is generated by a single X-ray photon.

In the apparatus for generating an X-ray image 100 according to the exemplary embodiment, any method among the aforementioned various methods may be applied in order to implement the X-ray detector 121. In addition, the exemplary embodiments are not limited to the aforementioned method. In addition to the aforementioned method, other methods in which X-rays are detected and are converted into an electrical signal, and an image signal is obtained may also be applied.

Hereinafter, a structure of the X-ray detector 121 to which the direct converting method of directly obtaining an electrical signal from X-rays and a hybrid method of combining a readout circuit chip and the light receiving element for detecting X-rays are applied will be described.

Figure 6:
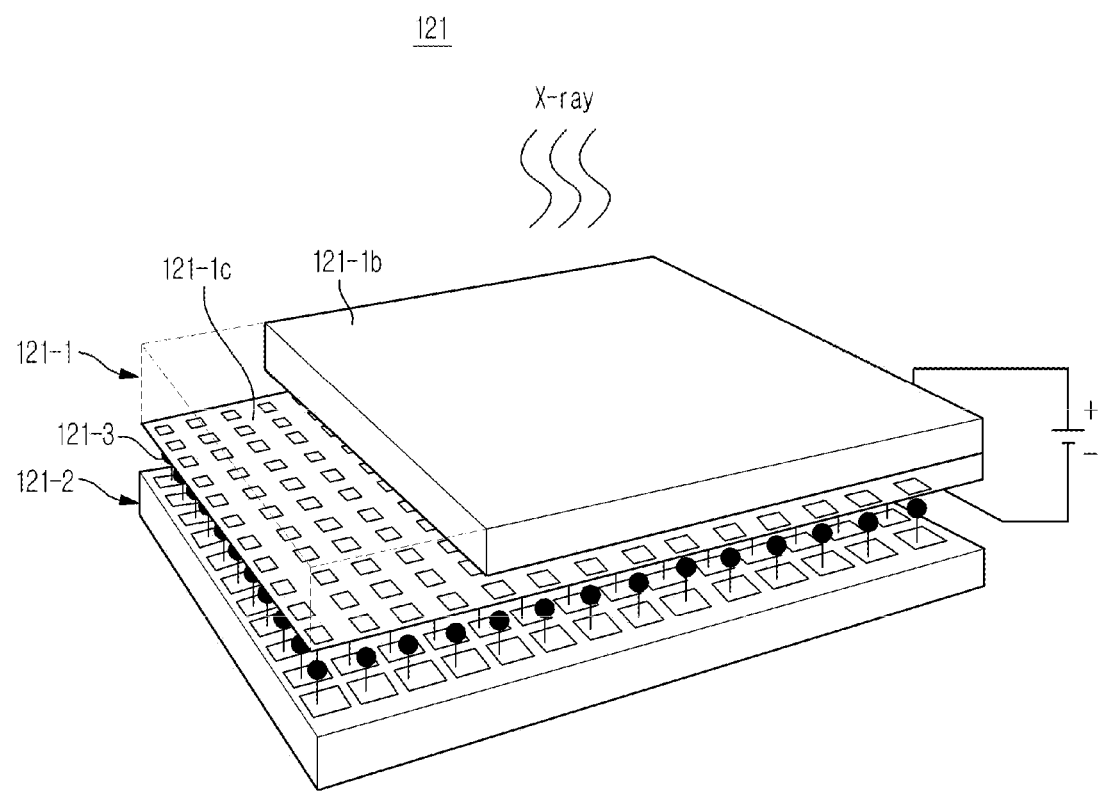
FIG. 6 is a diagram schematically illustrating a structure of an X-ray detector, in accordance with an exemplary embodiment.

As illustrated in FIG. 6, the X-ray detector 121 includes a light receiving element 121-1 that detects X-rays and converts the detected X-rays into an electrical signal and a readout circuit 121-2 that reads the electrical signal. Here, the readout circuit 121-2 is made in a two-dimensional (2D)-pixel array form including a plurality of pixel areas. In order to secure a high resolution, a rapid response time, and a high dynamic area with low energy and a small dose, a single crystal semiconductor material may be used as a material making up the light receiving element 121-1. Examples of the single crystal semiconductor material include germanium (Ge), cadmium telluride (CdTe), CdZnTe, and gallium arsenide (GaAs).

The light receiving element 121-1 may be formed as a PIN photodiode by bonding a p-type layer 121-1c in which p-type substrates are arranged in a 2D pixel array structure to a bottom of a high resistance n-type semiconductor substrate 121-1b. The readout circuit 121-2 using a CMOS process is connected to the light receiving element 121-1 for each pixel. The CMOS readout circuit 121-2 and the light receiving element 121-1 may be bonded using a flip-chip bonding method. The bonding may be performed using a method in which a bump 121-3, such as solder (PbSn) or indium (In) is formed and then is compressed through a reflow process. However, the aforementioned structure is only an example of the X-ray detector 121, and the structure of the X-ray detector 121 is not limited thereto.

Although not illustrated, an X-ray grid may be disposed in a front of the X-ray detector 121 in order to prevent scattering of X-rays.

When photons of X-rays are incident on the light receiving element 121-1, electrons in a valance band receive energy of photons, cross over a band gap energy difference, and are excited into a conduction band. Therefore, electron-hole pairs are generated in a depletion region.

When each metal electrode is formed in the p-type layer 121-1c and the n-type substrate 121-1b of the light receiving element 121-1 and a reverse bias is applied, electrons move to an n-type region and holes move to a p-type region among electron-hole pairs generated in the depletion region. The holes which are moved to the p-type region are input to the readout circuit 121-2 through bump bonding 121-3, which allows the electrical signal generated by the photons to be read. However, it is also possible to generate the electrical signal by inputting electrons to the readout circuit 121-2 according to an applied voltage and a structure of the light receiving element 121-1.

The readout circuit 121-2 may be formed in a 2D pixel array structure corresponding to the p-type semiconductor 121-1c of the light receiving element 121-1 and may read an electrical signal for each pixel. When electric charges are input to the readout circuit 121-2 from the light receiving element 121-1 through the bump bonding 121-3, the readout circuit 121-2 outputs an image signal that is represented as a voltage signal or the number of photons according to a circuit configuration thereof.

The image signal output from the X-ray detector 121 is input to the image processor 170. The image processor 170 may analyze and process the input image signal and generate an X-ray image of the breast.

As described above, the compression paddle 130 is configured to reduce the thickness of the breast serving as the object 30. In order to compress the object 30, the compression paddle 130 may move in a vertical direction. Since the reason for reducing the thickness of the object 30 using the compression paddle 130 has already been described in detail, a description thereof will not be repeated.

The driver 135 is configured to move the aforementioned compression paddle 130 in a vertical direction. In the exemplary embodiment, the driver 135 may be implemented as a motor type, a hydraulic type, a pneumatic type, or the like, but the exemplary embodiments are not limited thereto. That is, when a control signal for moving the compression paddle 130 is delivered from the controller 140 according to manipulation of the inputter 150 by the user, the driver 135 may move the compression paddle 130 up or down according to the delivered control signal.

The inputter 150 is configured to receive a command from the user. In the exemplary embodiment, a mouse, a keyboard, or the like may be used as the inputter 150, but the exemplary embodiments are not limited thereto. The display 160, which will be described below, and the inputter 150 may be implemented as an integrated touch panel.

The display 160 is configured to display an X-ray image processed by the image processor 170 and show the image to the user. In this case, the X-ray image may include a pre-shot X-ray image, a main shot X-ray image, and a finally generated diagnostic X-ray image which are to be described below, but the exemplary embodiments are not limited thereto.

In the exemplary embodiment, the display 160 may be implemented as a liquid crystal display (LCD), a light emitting diode (LED), an organic light emitting diode (OLED), a plasma display panel (PDP), or combinations thereof, but the exemplary embodiments are not limited thereto.

The user verifies the pre-shot X-ray image or the main shot X-ray image displayed in the display 160 by using the user's naked eye, manipulates the aforementioned inputter 150, and may set an interference target region in the pre-shot X-ray image or the main shot X-ray image.

The controller 140 is configured to control the overall operations of the apparatus for generating an X-ray image such that components constituting the apparatus for generating an X-ray image according to the exemplary embodiment are organically connected and operated.

This controller 140 may perform automatic exposure control (AEC). Here, the term "automatic exposure control" refers to a function of setting imaging conditions according to tissue characteristics of the object and adjusting exposure of the X-rays, that is, a strength, a radiation time, a radiation direction of X-rays, or the like. As described above, when the object is the breast, tissue characteristics of the object may include a thickness and a density of the breast.

In this case, as a method of verifying the thickness of the breast in the controller 140, for example, a method of verifying the thickness of the breast based on a value received from a sensor (not illustrated) which detects a position of the compression paddle 130 may be used or a method of verifying the thickness of the breast based on a monitoring result of operations of the driver 135 which move the compression paddle 130 may be used. However, the method of verifying the thickness of the breast in the controller 140 is not limited thereto.

In addition, the controller 140 may verify the breast density based on an image histogram of a pre-shot X-ray image obtained by performing pre-shot imaging on the object. Here, the image histogram is a graph illustrating a light and darkness distribution of the X-ray image, and may be generated in the image processor 170, which is further described below, and provided to the controller 140.

A method of verifying the breast density based on the image histogram in the controller 140 is described using the following example. First, the controller 140 integrates the entire image histogram, obtains an entire area of the breast, integrates parts having a brightness of a predetermined threshold value or more in the image histogram, and obtains an area of parenchymal tissues of the breast. Then, it is possible to calculate the breast density by multiplying a value obtained, by dividing the area of parenchymal tissues by the entire area, by 100.

When the tissue characteristics of the breast, that is, the thickness and the density, are verified through the aforementioned methods, the controller 140 finds an imaging condition corresponding to the verified tissue characteristic among imaging conditions previously stored in a storage 180, and sets a corresponding imaging condition as a main shot imaging condition. A main shot of the object 30 is imaged according to the imaging condition set in this manner. Here, the imaging condition may include the number of times imaging is performed, an imaging angle, an imaging position, tube voltage, tube current, a type of a material constituting the filter, and a type of a material constituting the anode, but the exemplary embodiments are not limited thereto.

In the exemplary embodiment, the controller 140 may set the interference target region in the pre-shot X-ray image or the main shot X-ray image of the object. The interference target may include a tissue that is not of interest among internal tissues of the object, a tool or a foreign material introduced into the inside of the object, but the exemplary embodiments are not limited thereto. The interference target region is a region including the interference target and a surrounding area of the interference target and designated by a user.

Here, the term "tissue that is not of interest" refers to a tissue having relatively low importance among internal tissues of the object, and may refer to, for example, a tissue such as a pectoral muscle connected to the breast in breast imaging. That is, it may be understood as a tissue that does not need to be diagnosed among internal tissues of the object included in the X-ray image. Moreover, the foreign material introduced inside of the object may include, for example, a prosthesis, but the exemplary embodiments are not limited thereto and may include any material that is located inside the object, but is not an original tissue of the object.

In the exemplary embodiment, the interference target region may be set manually or automatically.

Between these, the method of manually setting the interference target region may be a method in which the user manipulates the inputter 150 and designates a block in a corresponding part of the X-ray image. For example, when the mouse is used as the inputter 150, it is possible to set the interference target region so that the user sees the pre-shot X-ray image or the main shot X-ray image displayed in the display 160, verifies a part in which the interference target is located, moves the mouse to position a mouse pointer over a corresponding part, and clicks and drags the mouse to designate the corresponding part as a block. However, this is only an example, and it is apparent that the interference target region may be set using various methods according to the type of inputter 150.

The method of automatically setting the interference target region may be a method of setting the interference target region based on imaging information of the pre-shot X-ray image or the main shot X-ray image, a shape or a pattern of tissues, brightness characteristics of tissues, and information on a brightness change between tissues. Here, the imaging information may be imaging position information, but the exemplary embodiments are not limited thereto.

For example, when the object is the breast and the interference target is the pectoral muscle connected to the breast, the type of the obtained pre-shot X-ray image may include a right medio lateral oblique (RMLO) image, a left medio lateral oblique (LMLO) image, a right cranio caudal (RCC) image, and a left cranio caudal (LCC) image.

The controller 140 determines imaging information corresponding to the type of the obtained pre-shot X-ray image, determines a part in which the pectoral muscle serving as the interference target is located in the image by default according to the determined imaging information, analyzes a shape and a pattern of tissues of a corresponding part, brightness characteristics of the tissue, and information on a brightness change between tissues, and thus is able to set a rough interference target region according to the analyzed information.

For example, when the obtained pre-shot X-ray image is the RMLO image, the controller 140 determines that the pectoral muscle serving as a general interference target in the X-ray image of the breast is located in an upper right part in the image by default, analyzes a shape and a pattern of the tissue, brightness characteristics of the tissue, and information on a brightness change between tissues from a corner of the upper right part of the pre-shot X-ray image, and thus is able to set the interference target region including the pectoral muscle.

When it is difficult to determine a default position of the interference target as described above, the controller 140 analyzes a shape and a pattern of the tissue and brightness characteristics of the tissue as a whole X-ray image, compares whether the analyzed information corresponds to internal tissues of a general breast, detects a part having a difference, determines the part as the interference target, and is able to set the interference target region based on the information on a brightness change between tissues.

In addition, when there are two or more interference targets (for example, the pectoral muscle and the prosthesis) in the X-ray image, the controller 140 compares whether a shape and a pattern of the tissue and brightness characteristics of the tissue as a whole X-ray image correspond to internal tissues of a general breast, determines a part having a difference as the interference target, and then is able to set the interference target region using the information on a brightness change between tissues.

While the method of automatically setting the interference target region has been exemplified and described above, this is only an example and the method of automatically setting the interference target region is not limited thereto.

Figure 10:
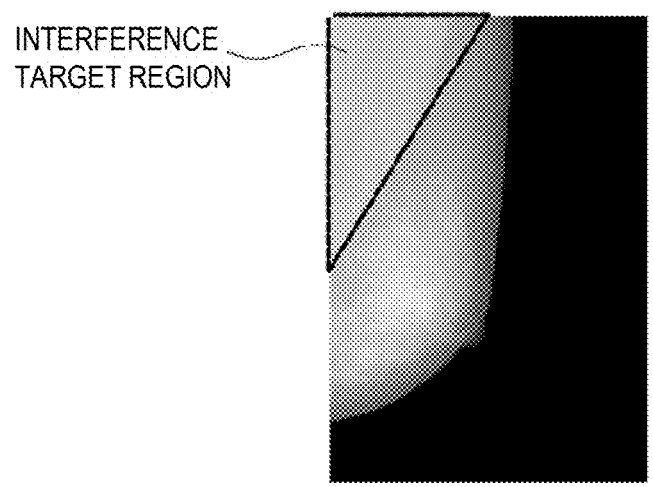
FIG. 10 is a diagram illustrating exemplary interference target region setting when there is one interference target, in accordance with an exemplary embodiment.
Figure 11:
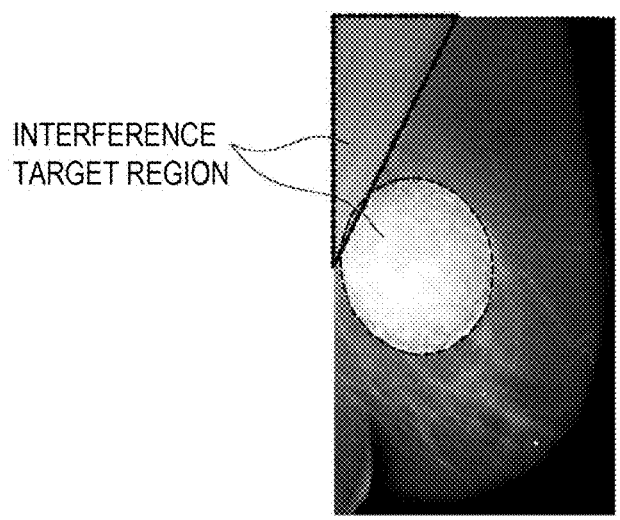
FIG. 11 is a diagram illustrating exemplary interference target region setting when there are a plurality of interference targets, in accordance with an exemplary embodiment.

FIGS. 10 and 11 illustrate examples in which the interference target region is set in the X-ray image using the aforementioned method. Here, the set interference target region is indicated by a dotted line. FIG. 10 illustrates a case in which there is an interference target. FIG. 11 illustrates a case in which there are two or more interference target regions as indicated by the dotted lines. In this case, FIG. 11 illustrates that interference target regions are set for all existing interference targets, but the exemplary embodiments are not limited thereto. It is also possible to set some of the many existing interference targets as the interference target region.

In addition, the controller 140 may set the main shot imaging condition based on an area other than the interference target region set as described above, that is, a region of interest. This is performed so that a main shot X-ray image is obtained in which a tissue of interest that requires diagnosis is clearly represented. That is, the main shot is performed using the imaging condition set based on characteristics of the tissue of interest located in the region of interest, and thus it is possible to obtain the main shot X-ray image in which the tissue of interest located in the region of interest is more clearly represented than the interference target.

In addition, position information in the X-ray image of the interference target region set using the above method may be stored in the storage 180.

That is, the apparatus for generating an X-ray image 100 according to the exemplary embodiment may further include the storage 180 that stores data as described above. That is, the storage 180 may store imaging conditions for each tissue characteristic of the object, the position information on the interference target region that is manually or automatically set in the X-ray image, or the like. The storage 180 may be implemented as a read only memory (ROM), a programmable ROM (PROM), an erasable PROM (EPROM), a non-volatile memory device such as a flash memory, a volatile memory device such as the RAM, or a storage medium such as a hard disk and an optical disc. However, the exemplary embodiments are not limited thereto and the storage 180 may also be implemented in any form known in the related art.

The image processor 170 is configured to read out an electrical signal from the X-ray detecting assembly 120, obtain an image signal, perform signal processing on the image signal, and generate the X-ray image.

First, as described above, the image processor 170 performs image analysis on the tissue of interest in an area other than the interference target region in the pre-shot X-ray image or the main shot X-ray image.

Specifically, after the pre-shot is performed, the image processor 170 may process the electrical signal that is read out from the X-ray detecting assembly 120 and generate the pre-shot X-ray image. After the main shot is performed, the image processor 170 may process the electrical signal that is read out from the X-ray detecting assembly 120 and generate the main shot X-ray image.

In addition, the image processor 170 may generate an image histogram of the generated pre-shot X-ray image and the generated image histogram may be provided to the controller 140. The generated pre-shot X-ray image may be provided to the display 160 and displayed.

The image processor 170 may perform image analysis on the tissue of interest in an area other than the set interference target region and obtain brightness information on the tissue of interest. That is, in the exemplary embodiment, the image analysis is performed on only a generally important tissue in the breast X-ray image such as a fat tissue, a mammary tissue, or the like.

As described above, the image processor 170 may perform image processing for optimizing the contrast between tissues on the entire main shot X-ray image based on the analyzed information as described above, specifically, brightness information on the tissue of interest, and may generate a final diagnostic X-ray image. That is, image processing is performed on the entire image using only analyzed information of tissues other than the interference target which can cause image quality degradation of the diagnostic image. Therefore, since information on the interference target does not influence the image processing, the image quality of the tissue of interest is relatively improved and it is possible to perform a more precise and accurate diagnosis.

Figure 12A:
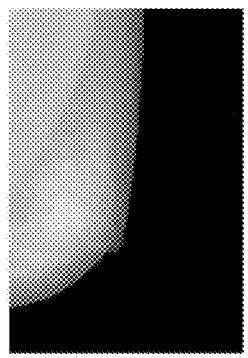
FIG. 12A is a diagram illustrating an X-ray image having an interference target, in accordance with an exemplary embodiment
Figure 12B:
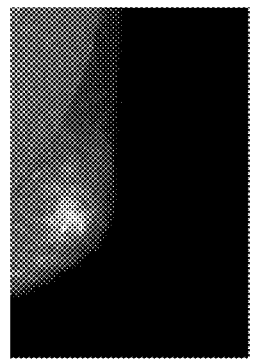
FIG. 12B is a diagram illustrating a final diagnostic X-ray image that is generated by performing image processing based on a tissue of interest, in accordance with an exemplary embodiment.

FIG. 12A illustrates an X-ray image having an interference target. FIG. 12B illustrates a final diagnostic X-ray image generated by performing image processing based on information on analysis of the tissue of interest. As illustrated in FIG. 12B, it can be seen that image quality of the tissue of interest part becomes more clear than that of FIG. 12A.

Each configuration of the apparatus for generating an X-ray image 100 according to the exemplary embodiment has been described. Hereinafter, a method of generating an X-ray image according to various exemplary embodiments will be described.

Figure 7:
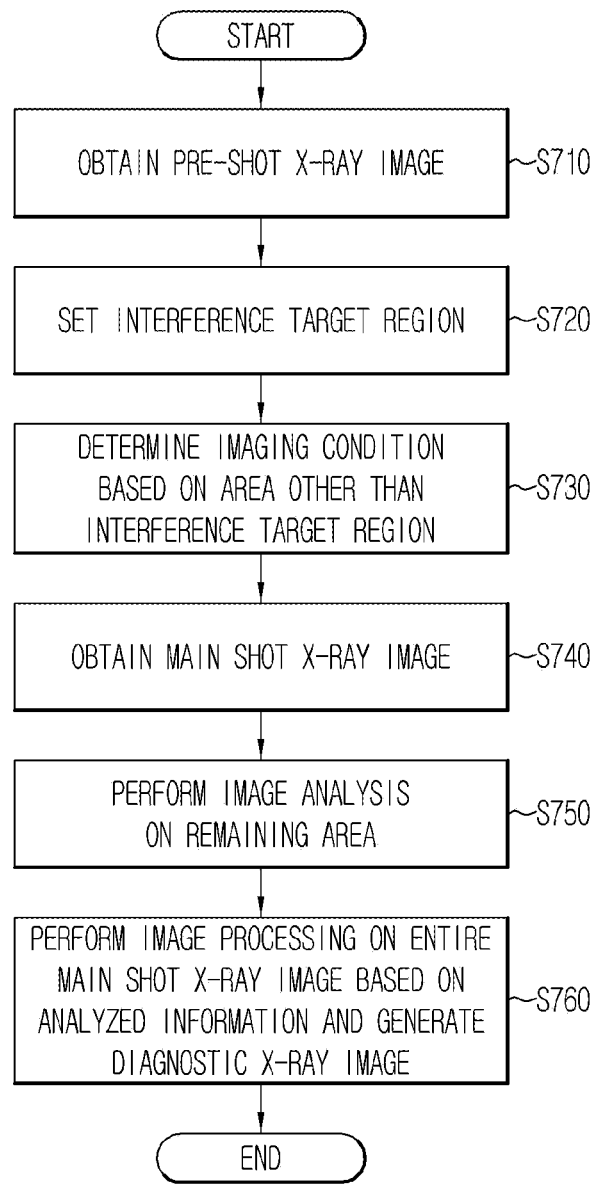
FIG. 7 is a flowchart sequentially illustrating a method of generating an X-ray image according to a first exemplary embodiment.

FIG. 7 is a flowchart sequentially illustrating a method of generating an X-ray image according to a first exemplary embodiment. The method of generating an X-ray image according to the first exemplary embodiment as illustrated in FIG. 7 is as follows.

First, pre-shot imaging is performed on the object 30, and a pre-shot X-ray image of the object is obtained (S710).

When the object 30 is, for example, a human breast, while a breast of a patient is placed on the breast contactor 123 of the X-ray detecting assembly 120, the breast is compressed by moving the compression paddle 130 down, the pre-shot imaging is performed and the pre-shot X-ray image is obtained.

Here, the term "pre-shot" imaging refers to imaging that is performed before a main shot imaging, to be described in more detail below, is performed. The pre-shot imaging is performed to verify tissue characteristics of the object and to set imaging conditions necessary for the main shot imaging according to the verified tissue characteristics. In this case, the term "shot" may be understood as a term indicating that X-rays are radiated. Further, the term "main shot," which will be described, refers to a shot that is performed according to the imaging condition set through the pre-shot imaging, and the X-ray image obtained by performing the main shot imaging may be used as the diagnostic X-ray image.

Although not illustrated in FIG. 7, in the exemplary embodiment, before the operation of obtaining the pre-shot X-ray image by performing the pre-shot imaging as described above, an operation of detecting a thickness of the breast compressed by the compression paddle 130 may be further included. In this case, the breast thickness may be detected based on a value received from a sensor for detecting a position of the compression paddle 130 or a monitoring result of operations of the driver 135 which moves the compression paddle 130, but the exemplary embodiments are not limited thereto.

Moreover, in this operation, after the pre-shot imaging is performed, the pre-shot X-ray image may be generated by the image processor 170 obtaining an image signal by reading an electrical signal from the X-ray detecting assembly 120 and performing signal processing on the image signal.

Furthermore, although not illustrated in FIG. 7, after the operation of obtaining the pre-shot X-ray image, an operation in which the image processor 170 forms an image histogram of the obtained pre-shot X-ray image and a breast density is determined based on the formed image histogram may be further included.

Next, the interference target region in the obtained pre-shot X-ray image is set (S720).

Here, the interference target may include a tissue that is not of interest among internal tissues of the object, a foreign material introduced inside of the object, or the like, but the exemplary embodiments are not limited thereto.

Here, the term "tissue that is not of interest" refers to a tissue having relatively low importance among internal tissues of the object, and may refer to, for example, the pectoral muscle connected to the breast in breast imaging. That is, it may be understood as a tissue that does not need to be diagnosed among internal tissues of the object included in the X-ray image. Moreover, the foreign material introduced into the inside of the object may include, for example, a prosthesis, but the exemplary embodiments are not limited thereto and may include any material that is located inside the object but is not an original tissue of the object.

In this operation, the interference target region may be set manually or automatically.

Between the settings, the method of manually setting the interference target region may refer to performing direct manipulation by the user. Specifically, the user verifies the pre-shot X-ray image displayed in the display 160 with the naked eye, and directly designates a part determined as the interference target using the inputter 150. For example, when the mouse is used as the inputter 150, it is possible to manually set the interference target region by the user moving the mouse so as to position a mouse pointer over a part determined as the interference target, and clicking and dragging the mouse to designate a block.

The method of manually setting the interference target region has been exemplified and described, but this is only an example, and the method of manually setting the interference target region is not limited thereto.

The method of automatically setting the interference target region may be performed by the controller 140. For example, the interference target region may be automatically set using a shape and a pattern of the tissue, brightness characteristics of the tissue, and information on a brightness change between tissues based on imaging information of the object.

Here, the imaging information of the object may be imaging position information, but the exemplary embodiments are not limited thereto.

When the object 30 is a human breast and the interference target is the pectoral muscle, it is determined whether a type of the obtained pre-shot X-ray image is a right medio lateral oblique (RMLO) image, a left medio lateral oblique (LMLO) image, a right cranio caudal (RCC) image, or a left cranio caudal (LCC) image. After a part in which the pectoral muscle serving as the interference target is located is determined by default according to the determined imaging position information, the interference target region is set using a shape and a pattern of tissues of a corresponding part, brightness characteristics of the tissues, and information on a brightness change between tissues.

For example, when it is determined that the obtained pre-shot X-ray image is the RMLO image, the controller 140 determines that the pectoral muscle serving as the interference target is located in an upper right part in the image by default, compares a shape and a pattern of the tissue, brightness characteristics of the tissue, and information on a brightness change between tissues from a corner of the upper right part of the pre-shot X-ray image, and is able to set the interference target region including the pectoral muscle.

The method of automatically setting the interference target region has been exemplified and described above, but this is only an example and the method of automatically setting the interference target region is not limited thereto.

Next, a main shot imaging condition is determined based on characteristics of the tissue of interest in an area other than the interference target region set in the pre-shot X-ray image (S730), the main shot imaging is performed according to the determined imaging condition, and the main shot X-ray image is obtained (S740).

Specifically, the controller 140 analyzes characteristics (for example, a density) of the tissue of interest based on the image histogram of the pre-shot X-ray image provided from the image processor 170, and then may determine the main shot imaging condition corresponding to the analyzed tissue characteristics. Here, the imaging condition may include the number of times imaging is performed, an imaging angle, an imaging position, tube voltage, tube current, a type of a material constituting the filter, a type of a material constituting the anode, or the like, but the exemplary embodiments are not limited thereto.

That is, when the main shot imaging condition is determined, tissue characteristics of the interference target are not referred to but only characteristics of the tissue of interest are referred to. In this manner, since the main shot imaging is performed according to the imaging condition set based on the tissue of interest, it is possible to obtain the main shot X-ray image in which the tissue of interest is relatively clear compared to the interference target.

Next, image analysis is performed on the tissue of interest in an area other than the interference target region in the obtained main shot X-ray image (S750), image processing is performed on the entire main shot X-ray image based on the analyzed information, and a diagnostic X-ray image is generated (S760).

That is, the interference target is excluded from the obtained main shot X-ray image, the image analysis is performed on only the tissue of interest for which diagnosis is necessary, image processing for optimizing contrast between tissues is performed on the entire main shot X-ray image based on the analyzed information on the tissue of interest, and a final diagnostic X-ray image is generated.

Therefore, precision and accuracy of the tissue of interest having relatively high importance increase, and the diagnostic X-ray image in which the tissue of interest becomes clearer may be generated, which results in accurate diagnosis.

Figure 8:
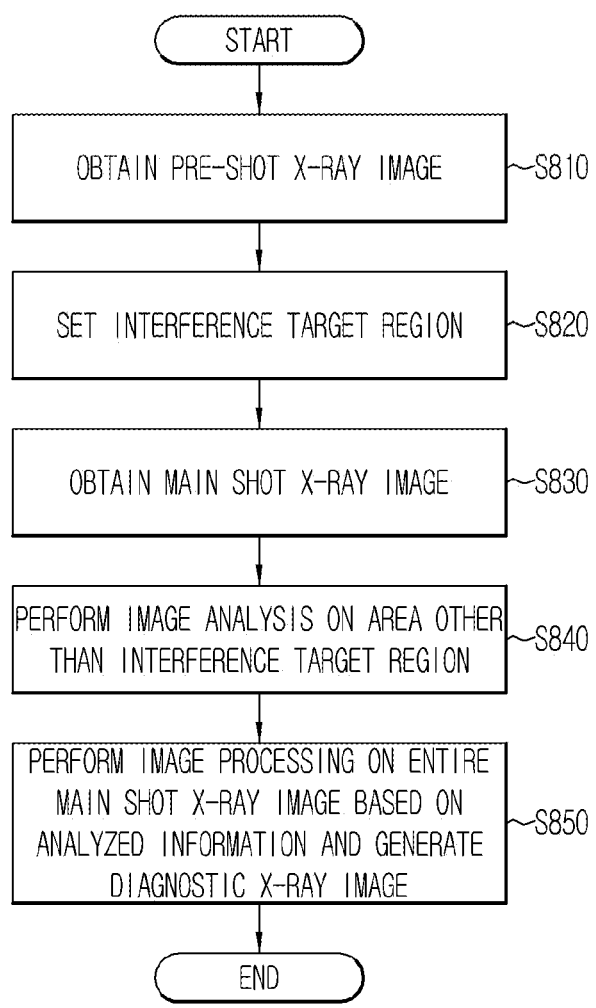
FIG. 8 is a flowchart sequentially illustrating a method of generating an X-ray image according to a second exemplary embodiment.

FIG. 8 is a flowchart sequentially illustrating a method of generating an X-ray image according to a second exemplary embodiment. In the exemplary embodiment, detailed description of configurations corresponding to the aforementioned first exemplary embodiment will be omitted.

The method of generating an X-ray image according to the exemplary embodiment as illustrated in FIG. 8 is as follows.

First, pre-shot imaging is performed on the object 30 and a pre-shot X-ray image of the object is obtained (S810).

That is, when the object 30 is, for example, a human breast, while a breast of a patient is on the breast contactor 123 of the X-ray detecting assembly 120, the breast is compressed by moving the compression paddle 130 down, the pre-shot is performed and the pre-shot X-ray image is obtained.

Next, the interference target region in the obtained pre-shot X-ray image is set (S820).

In this operation, the interference target region may be manually set by the user manipulating the inputter 150 as described above, or may be automatically set using a shape and a pattern of the tissue, brightness characteristics of the tissue, and information on a brightness change between tissues based on the imaging information of the pre-shot X-ray image. Since this has already been described in detail, a description thereof will not be repeated.

Next, the main shot imaging is performed on the object 30 and the main shot X-ray image is obtained (S830).

The imaging condition of the main shot performed in this operation may be determined so as to correspond to tissue characteristics of the object that are analyzed based on the image histogram of the entire pre-shot X-ray image obtained through the operation of S810. That is, the tissue characteristics of the object in the pre-shot X-ray image are determined based on the image histogram, and the imaging condition is determined according to the determined tissue characteristics.

In this manner, this exemplary embodiment is different from the aforementioned first exemplary embodiment in that the imaging condition of the main shot imaging is determined based on the image histogram of the entire pre-shot X-ray image.

Next, image analysis is performed on only the tissue of interest in an area other than the interference target region set through the operation of S820 in the obtained main shot X-ray image (S840), image processing is performed on the entire main shot X-ray image based on the analyzed information on the tissue of interest, and a diagnostic X-ray image is generated (S850).

Figure 9:
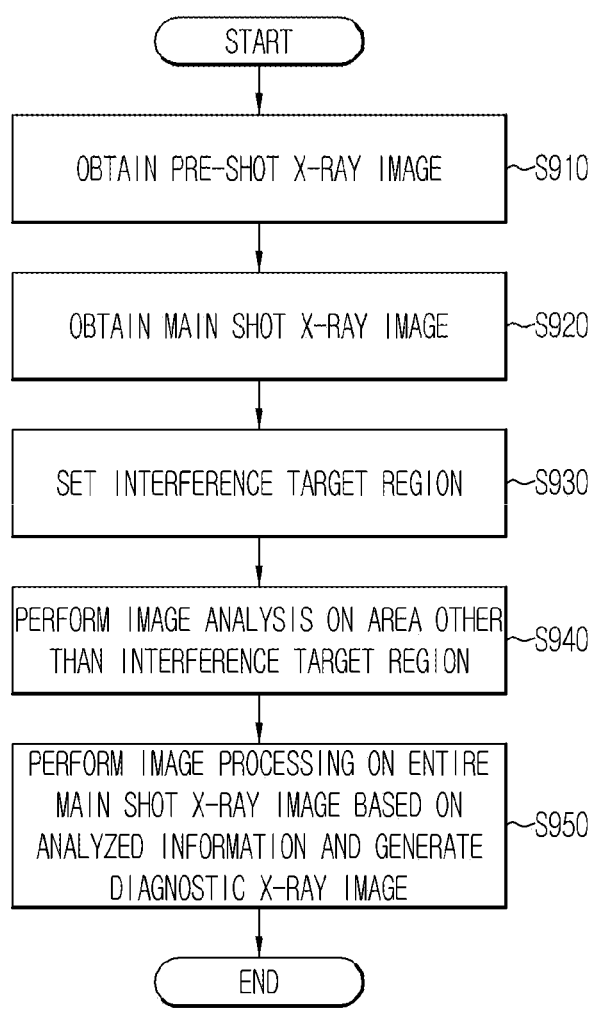
FIG. 9 is a flowchart sequentially illustrating a method of generating an X-ray image according to a third exemplary embodiment.

FIG. 9 is a flowchart sequentially illustrating a method of generating an X-ray image according to a third exemplary embodiment. In this exemplary embodiment, detailed description of configurations corresponding to the aforementioned first exemplary embodiment or second exemplary embodiment will be omitted.

The method of generating an X-ray image according to the exemplary embodiment as illustrated in FIG. 9 is as follows.

First, pre-shot imaging is performed on the object 30 and a pre-shot X-ray image of the object is obtained (S910).

That is, when the object 30 is, for example, a human breast, while a breast of a patient is placed on the breast contactor 123 of the X-ray detecting assembly 120, the breast is compressed by moving the compression paddle 130 down, the pre-shot imaging is performed and the pre-shot X-ray image is obtained.

Next, the main shot imaging is performed on the object 30 and the main shot X-ray image of the object 30 is obtained (S920).

The imaging condition of the main shot imaging performed in this operation may be determined based on the image histogram of the entire pre-shot X-ray image obtained through the operation of S810. That is, tissue characteristics of the object in the pre-shot X-ray image are determined using the image histogram, and the imaging condition is determined according to the determined tissue characteristics.

Next, the interference target region is set in the main shot X-ray image obtained through the operation of S920 (S930).

In this operation, the interference target region may be set manually or automatically as described above. Since the methods of setting manually and automatically have already been described, description thereof will not be repeated.

That is, in the aforementioned first exemplary embodiment and second exemplary embodiment, the interference target region is set before the main shot X-ray image is obtained. However, this exemplary embodiment is different from the aforementioned first exemplary embodiment and second exemplary embodiment in that the interference target region is set after the main shot X-ray image is obtained.

Next, image analysis is performed on the tissue of interest in an area other than the interference target region set through the operation of S930 in the main shot X-ray image obtained through the operation of S920 (S940), image processing is performed on the entire main shot X-ray image based on the analyzed information, and a diagnostic X-ray image is finally generated (S950).

The exemplary embodiments have been described above. In the aforementioned exemplary embodiments, some components of the apparatus for generating an X-ray image may be implemented as a kind of module. Here, the term "module" refers to software or a hardware component such as a field programmable gate array (FPGA) or an application specific integrated circuit (ASIC), and the module can perform certain functions. However, the module is not limited to software or hardware. The module may be configured in a recording medium that can be addressed or may be configured to execute at least one processor.

Examples of the module may include software components, object-oriented software components, class components, components such as task components, processes, functions, properties, procedures, subroutines, segments in program codes, drivers, firmware, microcode, circuits, data, databases, data structures, tables, arrays, and variables. Components and functions provided from modules may be combined into a smaller number of components and modules or may be further separated into additional components and modules. In addition, the components and modules may execute at least one CPU in a device.

In addition to the aforementioned exemplary embodiments, some of the exemplary embodiments may be implemented through a medium including a computer readable code or instruction for controlling at least one processing component of the aforementioned exemplary embodiment, for example, a computer readable recording medium. The medium may correspond to a medium or media which enable the computer readable code to be stored and/or transmitted.

The computer readable code may be recorded in the medium or transmitted via the Internet. The medium may include, for example, recording media including a magnetic recording medium (for example, a ROM, a RAM, a floppy disk, and a hard disk), an optical recording medium (for example, a CD-ROM or a DVD), and a transmitting medium such as a carrier wave. Moreover, according to the exemplary embodiments, the medium may also include a signal such as a synthesizing signal or a bitstream. The medium may be a distributed network and thus the computer readable code may be stored, transmitted, or executed in a distributed manner. Moreover, examples of the processing component may include a processor or a computer processor, and the processing component may be distributed and/or included in a single device.

In the exemplary embodiments, image processing is performed on the entire X-ray image based on analyzed information of the tissue of interest in an area other than the interference target region in the X-ray image. Therefore, high precision and accuracy are given to the tissue of interest having relatively high importance and it is possible to generate a high quality diagnostic X-ray image.

The exemplary embodiments have been described in detail above, however, the exemplary embodiments should be considered in a descriptive sense only, and the exemplary embodiments are not limited thereto. It will be apparent to those skilled in the art that various modifications and improvements within the scope of an exemplary embodiment may be made.

Simple modifications and alterations of the exemplary embodiments fall within the scope of an exemplary embodiments and the scope of the exemplary embodiments are defined by the appended claims.

What is claimed is:

1. A method of generating an X-ray image, the method comprising:
obtaining the X-ray image of an object which includes a tissue of interest and an interference target region that are disposed together within the object, the obtaining the X-ray image of the object including:
obtaining a pre-shot X-ray image of the object by radiating X-rays onto the object,
setting an imaging condition based on tissue characteristics of the object in an area of the object other than the interference target region, in the pre-shot X-ray image, and
obtaining a main shot X-ray image of the object by radiating the X-rays being generated based on the imaging condition which has been set through the pre-shot X-ray image;
performing an image analysis on the tissue of interest in the area of the object other than the interference target region, in the main shot X-ray image;
applying image processing to an entirety of the main shot X-ray image based on information on the image analysis of the tissue of interest, the entirety of the main shot X-ray image including the tissue of interest and the interference target region; and
generating a final X-ray image based on the main shot X-ray image to which the image processing has been applied.

2. The method according to claim 1, wherein the obtaining the X-ray image of the object further comprises:
setting the interference target region in the pre-shot X-ray image.

3. The method according to claim 2, wherein the setting the interference target region is performed by designating a block area in the pre-shot X-ray image which includes an interference target.

4. The method according to claim 2, wherein, in the setting the interference target region, a default position of an interference target is determined based on imaging information of the pre-shot X-ray image and the setting is performed based on a shape and a pattern of tissues in the determined default position, brightness characteristics of the tissues, and a brightness change between the tissues.

5. The method according to claim 1, wherein the applying the image analysis to the tissue of interest comprises:
detecting brightness information of each pixel making up the tissue of interest included in the main shot X-ray image.

6. The method according to claim 5, wherein the generating the final X-ray image comprises:
adjusting a contrast between tissues in the entirety of the main shot X-ray image based on the detected brightness information.

7. An apparatus for generating an X-ray image, the apparatus comprising:
an X-ray source configured to generate X-rays and to radiate the X-rays onto an object which includes a tissue of interest and an interference target region which are disposed together within the object;
an X-ray detecting assembly configured to detect the X-rays having been transmitted through the object and to convert the detected X-rays into electrical signals; and
an image processor configured to generate a pre-shot X-ray image of the object based on the electrical signals, to set an imaging condition based on tissue characteristics of the object in an area of the object other than the interference target region in the pre-shot X-ray image, to generate a main shot X-ray image of the object based on the electrical signals which are generated when the X-rays are generated and detected based on the imaging condition which has been set through the pre-shot X-ray image, to perform an image analysis on the tissue of interest in the area of the object other than the interference target region in the main shot X-ray image, to apply an image processing on an entirety of the main shot X-ray image based on analyzed information obtained from the image analysis, the entirety of the main shot X-ray image including the tissue of interest and the interference target region, and to generate a final X-ray image based on the main shot X-ray image to which the image processing has been applied.

8. The apparatus according to claim 7, further comprising a controller configured to set the interference target region in the pre-shot X-ray image.

9. The apparatus according to claim 8, wherein the controller sets the interference target region by designating a block area in the pre-shot X-ray image which includes an interference target.

10. The apparatus according to claim 8, wherein the controller determines a default position of an interference target based on imaging information of the pre-shot X-ray image and sets the interference target region based on a shape and a pattern of tissues in the determined default position, brightness characteristics of the tissues, and a brightness change between the tissues.

11. The apparatus according to claim 7, wherein the interference target region is set in the pre-shot X-ray image.

12. The apparatus according to claim 11, wherein, after the interference target region is set in the pre-shot X-ray image and the imaging condition is set based on the tissue characteristics in the area other than the interference target region in the pre-shot X-ray image, the X-rays corresponding to the set imaging condition are radiated onto the object, and the main shot X-ray image is obtained.

13. A method of generating an X-ray image of an object, the method comprising:
obtaining a pre-shot X-ray image of the object by radiating X-rays into the object;
identifying, in the pre-shot X-ray image, an interference target which is disposed within the object together with a tissue of interest;
setting, in the pre-shot X-ray image, an interference target region which surrounds the interference target;
setting an imaging condition based on tissue characteristics of the object in an area of the object other than the interference target region in the pre-shot X-ray image;
obtaining a main shot X-ray image of the object by radiating the X-rays being generated based on the imaging condition which has been set through the pre-shot X-ray image;
performing an image analysis on the tissue of interest in the area of the object other than the interference target region in the main shot X-ray image;

applying image processing to an entirety of the main shot X-ray image based on the image analysis of the tissue of interest, the entirety of the main shot X-ray image including the tissue of interest and the interference target region; and
generating a final X-ray image of the object based on the main shot X-ray image to which the image processing has been applied, the final X-ray image showing the tissue of interest and the interference target region disposed together within the object which has been X-ray imaged.

14. The method according to claim 1, wherein the tissue of interest is a breast tissue, and
the interference target region includes at least one among a foreign object implanted in a breast and a pectoral muscle connected to the breast tissue.

* * * * *